United States Patent
Llewellyn

(12) 
(10) Patent No.: US 6,451,782 B1
(45) Date of Patent: Sep. 17, 2002

(54) USE OF 4-ANDROSTENE-3ALPHA,17 BETA-DIOL TO INCREASE TESTOSTERONE LEVELS IN HUMANS

(76) Inventor: William Charles Llewellyn, P.O. Box 1162, Sound Beach, NY (US) 11789

( * ) Notice: Subject to any disclaimer, the term of this patent is extended or adjusted under 35 U.S.C. 154(b) by 0 days.

(21) Appl. No.: 10/075,038

(22) Filed: Feb. 12, 2002

(51) Int. Cl.[7] ........................ A61K 31/568; A61L 37/00; A61P 15/00; A61P 5/26
(52) U.S. Cl. ........................................ 514/182; 424/449
(58) Field of Search ........................ 514/182; 424/464, 424/451, 449

(56) References Cited

U.S. PATENT DOCUMENTS 5,880,117 A * 3/1999 Arnold ........................ 514/178

\* cited by examiner

*Primary Examiner*—Edward J. Webman
*Assistant Examiner*—Helen Nguyen

(57) ABSTRACT

This invention discloses methods of administering 4-Androstene-3alpha,17beta-diol in order to increase testosterone levels in humans. As men age, a decline in androgenic hormone levels is typically noted, possibly resulting in muscle mass, bone density and energy loss. Various methods have therefore been developed to supplement androgens for men with declining levels. Some such have focused on the use of direct metabolic precursors to testosterone, as a means of raising levels of this androgen in humans. This invention is an improvement over the use of the precursor 4-Androstene-3,17-beta-diol, in that the subject of this invention displays a much higher ability to convert to testosterone in the human body. This may be a very advantageous trait for aging men who require a safe and effective way to treat subnormal androgen levels.

4 Claims, No Drawings

USE OF 4-ANDROSTENE-3ALPHA,17 BETA-DIOL TO INCREASE TESTOSTERONE LEVELS IN HUMANS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Testosterone is considered to be the primary male androgen. It is responsible for the development and maintenance of male sexual characteristics, including external virilization, sexual maturity at puberty, spermatogenesis, sexual behavior/libido and erectile functioning. It also supports bone and muscle tissue growth, and remains vital to ones health and well being throughout life. After physical maturity, men often notice a slow decline in the level of testosterone produced by the body. Dubbed andropause, subnormal androgen levels can lead to a decline in muscle mass, libido, sexual functioning and overall sense of well being later in life. In many instances this indicates a need for some form of androgen replacement.

A number of methods have been developed to restore androgen concentration in humans with declining levels. Several injectable esterified testosterone preparations have been fashioned that allow a slow release of hormone into the blood stream over the course of several days to weeks for example, however all provide inconsistent dosing as there is great variance in hormone release from the site of injection, such that a short supraphysiological rush may eventually be followed by days of subnormal hormone concentrations. The buildup of estrogens due to the natural process of aromatization may exaggerate the side effects to such medication, particularly at times when testosterone levels are abnormally high, as supraphysiological levels of estrogens in the male body have been linked to gynecomastia (female breast tissue development), water retention and edema, and increased fat deposition.

Also a number of synthetic oral androgen derivatives have been developed including methyltestosterone, fluoxymesterone and stanozolol. All such compounds are alkylated at the $17^{th}$ carbon position (alpha orientation), an alteration that inhibits reduction of the steroid to inactive 17-ketosteroid form. While this greatly improves oral bioavailability of the compound, this alteration has also been shown to place stress on the liver, in some instances resulting in organ damage. Although the use of a c-17 alpha alkylated oral androgen may prove much more comfortable for the patient in terms of dosing and control over blood hormone level compared to an injectable preparation, the possible risk of developing complications with liver functions may make them much less useful for androgen replacement compared to injectable preparations, particularly for extended periods of therapy.

In searching for a less toxic, more reliable oral alternative for androgen replacement the use of androgen precursor hormones have been suggested. U.S. Pat. No. 5,880,117 to Patrick Arnold relates a method of using the precursor hormone 4-androstene-3,17beta-diol as a means of increasing testosterone levels in humans. The pharmacokinetics of administering such a precursor are such that hormone concentrations of active hormone (testosterone) peak within 90 minutes, and subsequently decline over a period of three to four hours. This more closely resembles the natural pulsating pattern in which the body releases testosterone, and avoids the prolonged peaks and troughs noted with use of esterified injectable hormone preparations. Although the precursor hormone 4-androstene-3,17beta-diol discussed in this patent has been shown to effectively convert to testosterone after administration and represents a great improvement over previous androgen replacement methods, it is also not the most ideal isomer of this hormone to use for this purpose. U.S. Pat. No. 5,880,117 to Patrick Arnold specifically excludes the 3-alpha isomer 4-androstene-3alpha, 17beta-diol in its scope, which according to this invention is a much more active precursor to the testosterone molecule than the 3-beta.

BRIEF SUMMARY OF THE INVENTION

U.S. Pat. No. 5,880,117 relates a novel method of using a direct precursor hormone to testosterone as a means of replacing androgen levels in men. Although the suggested practice of using a precursor to the active steroid testosterone seems quite sound, the precursor in this patent (4-androstene-3,17beta-diol) is not extremely active at converting to testosterone in the human body. The problem of the present invention is therefore to provide another precursor to testosterone that can be used to replace androgen action in humans, but with a much greater level of efficacy. According to the invention this problem is solved by the use of 4-androstene-3alpha, 17beta-diol. The mentioned androgen precursor hormone is ideal because it demonstrates a much more complete level of conversion to testosterone in human.

BRIEF DESCRIPTION OF THE SEVERAL VIEWS OF THE DRAWING

Not Applicable

DETAILED DESCRIPTION OF THE INVENTION

4-Androstene-3alpha, 17beta-diol has been identified as a direct metabolite of testosterone in human placental, uterine, testicular, adrenal and nervous system tissues. 4Androstene-3alpha, 17beta-diol also acts as precursor to testosterone in humans, converting to this active androgen via the 3alpha-hydroxysteroid-dehydrogenase enzyme.

Tests carried out by Ungar, Gut and Dorfman (J. Biol Chem 1957 v.224 191) have fundamentally proven the rapid biotransformation of 4-androstene-3alpha, 17beta-diol into testosterone in-vitro. In this study 4-androstene-3, 17beta-diol and 4-androstene-3alpha, 17beta-diol were incubated with rat and chicken liver preparations, and the formed metabolites were identified. The identified metabolites of both compounds included androstenedione, epitestosterone and testosterone. This investigation clearly demonstrated that like 4-Androstene-3, 17beta-diol, 4-Androstene-3alpha, 17beta-diol shares a metabolic pathway to the androgen testosterone.

Further in-vivo experiments by Kundu, Sandberg and Slaunwhite (Steroids November 1965 p 543–51) demonstrate the direct precursor relationship of 4-Androstene-3alpha, 17beta-diol to testosterone in humans. Here radiolabeled 4-Androstene-3alpha, 17beta-diol and 4-Androstene-3, 17beta-diol were injected intravenously into humans, and their urinary metabolites identified. The labeling specifically allowed the investigators to identify whether or not the allylyic 3-alpha hydroxyl group on 4-Androstene-3alpha, 17beta-diol would covert to the 3-keto group necessary to form testosterone. The investigators here note that they have led to the same conclusions as the Ungar experiment, with both 4-Androstene-3alpha, 17beta-diol and 4-Androstene-3, 17beta-diol metabolized by the same pathway and sharing a direct precursor relationship to testosterone. Of further interest was that this experiment fundamentally proved that the sole pathway of metabolism of the 4-Androstene-3alpha, 17beta-diol to its unsaturated (androstane) metabolites involved first its conversion to a 3-keto steroid.

It was the intention of this researcher to show that the advantages of 4-androstene-3, 17-beta-diol as a testosterone elevating agent can also be achieved with 4-Androstene-3alpha, 17beta-diol. In an effort to prove this theory a clinical study was therefore undertaken by the inventor. Specifically it was the intention of the inventor to investigate whether 4-Androstene-3alpha, 17beta-diol would act as an effective in-vivo peroral testosterone precursor in man.

Oral 4-Androstene-3alpha, 17beta-diol can be given in daily doses of 25 mg. to 1000 mg.; preferably 100 to 500 mg. These daily doses can be divided into several subdoses with 3–5 being most preferable. In addition to peroral administration, 4-Androstene-3alpha, 17beta-diol can also be effectively administered by several other routes including transdermal, intranasal and sublingual. A particular advantageous method of sublingual administration involves complexing 4-Androstene-3alpha, 17beta-diol with beta-hydroxypropyl-beta-cyclodextrin, which is then pressed into tablets.

I claim:

1. A method of increasing the testosterone level in man, said method comprising administering to said individual an effective amount consisting essentially of 4-Androstene-3alpha,17beta-diol.

2. The method of claim 1 wherein said administration is peroral.

3. The method of claim 1 wherein said administration is selected from the group consisting of transdermal, intranasal, and sublingual.

4. The method of claim 1, wherein said amount is a daily dosage of 25 to 1000 mg.

* * * * *